United States Patent [19]

Dunfee

[11] Patent Number: 5,724,993
[45] Date of Patent: *Mar. 10, 1998

[54] INFLATABLE SPINAL TRACTION DEVICE

[75] Inventor: Matthew J. Dunfee, Jordan, Minn.

[73] Assignee: Antigee Advantage International, Inc., Minneapolis, Minn.

[*] Notice: The term of this patent shall not extend beyond the expiration date of Pat. No. 5,704,904.

[21] Appl. No.: 580,708

[22] Filed: Dec. 29, 1995

Related U.S. Application Data

[63] Continuation-in-part of Ser. No. 474,780, Jun. 7, 1995, abandoned.

[51] Int. Cl.$^6$ ............................................. A61F 5/37
[52] U.S. Cl. ........................... 128/874; 602/13; 602/19
[58] Field of Search ................................... 128/845, 846, 128/882, DIG. 20; 602/5, 13, 19; 2/2

[56] References Cited

U.S. PATENT DOCUMENTS

| | | | |
|---|---|---|---|
| 1,589,670 | 6/1926 | Vartia | 128/DIG. 20 |
| 3,186,405 | 6/1965 | Bailey . | |
| 3,868,952 | 3/1975 | Hatton . | |
| 3,993,056 | 11/1976 | Rabischong | 128/DIG. 20 |
| 4,269,179 | 5/1981 | Burton et al. . | |
| 4,497,517 | 2/1985 | Gmeiner et al. . | |
| 4,552,135 | 11/1985 | Racz et al. . | |
| 4,559,933 | 12/1985 | Batard et al. . | |
| 4,622,957 | 11/1986 | Curlee . | |
| 4,624,248 | 11/1986 | Poole | 128/DIG. 20 |
| 4,682,588 | 7/1987 | Curlee | 128/DIG. 20 |
| 4,685,668 | 8/1987 | Newlin, Jr. . | |
| 4,691,696 | 9/1987 | Farfan de los Godos . | |
| 4,702,235 | 10/1987 | Hong . | |
| 4,768,499 | 9/1988 | Kemp . | |
| 4,898,185 | 2/1990 | Fuller . | |
| 4,960,115 | 10/1990 | Ranciato . | |
| 4,991,572 | 2/1991 | Chases . | |
| 4,991,573 | 2/1991 | Miller . | |
| 5,060,639 | 10/1991 | Marcus . | |
| 5,062,414 | 11/1991 | Grim . | |
| 5,076,264 | 12/1991 | Lonardo et al. . | |
| 5,101,815 | 4/1992 | Langdon-Orr . | |
| 5,111,807 | 5/1992 | Spahn et al. . | |
| 5,135,471 | 8/1992 | Houswerth . | |
| 5,188,586 | 2/1993 | Castel et al. . | |
| 5,256,135 | 10/1993 | Avihod . | |
| 5,338,289 | 8/1994 | Cooker . | |
| 5,382,226 | 1/1995 | Graham . | |
| 5,403,266 | 4/1995 | Bragg et al. . | |
| 5,441,479 | 8/1995 | Chitwood . | |

OTHER PUBLICATIONS

AliMed Catalog 1993, p. 28.
Flaghouse Rehab Catalog 1993, p. 39.
The Saunders Group, Inc. Catalog, p. 37.

Primary Examiner—Michael A. Brown
Attorney, Agent, or Firm—Patterson & Keough, P.A.

[57] ABSTRACT

Disclosed herein is an inflatable spinal traction device capable of both preventing spinal injuries, and of facilitating the healing of existing spinal injuries. As disclosed, the device of the present invention includes an upper horizontal support member, a lower horizontal support member, and a plurality of vertical support members fixedly attached at each end to the upper and lower members, wherein each of the vertical support members contains therein an inflatable bladder in fluid connection to an inflation means.

13 Claims, 9 Drawing Sheets

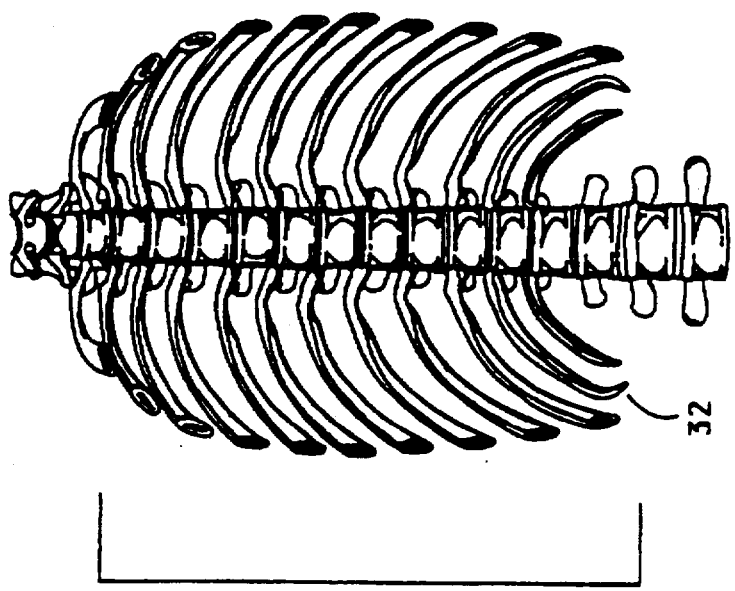
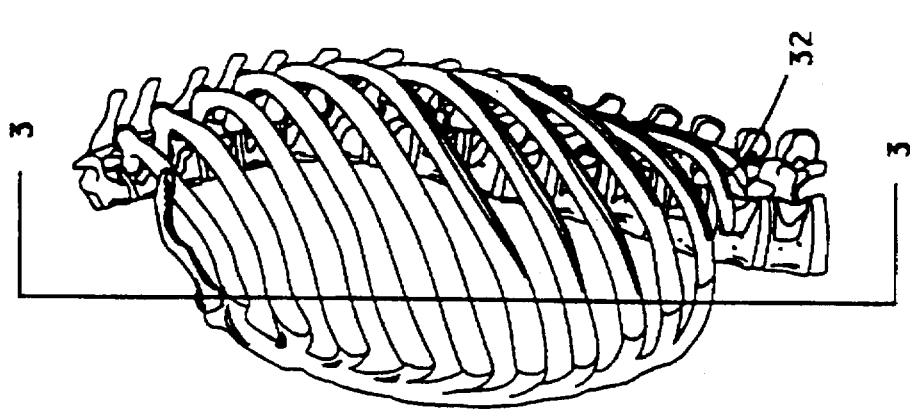
Fig. 3B
Fig. 3A

INFLATABLE SPINAL TRACTION DEVICE

CROSS-REFERENCE TO RELATED APPLICATIONS

This is a continuation-in-part of application Ser. No. 08/474,780, filed Jun. 7, 1995, now abandoned.

FIELD OF THE INVENTION

This invention relates in general to devices to aid in the healing of spinal injuries or to support various spinal regions to prevent the occurrence or re-occurrence of injuries.

BACKGROUND OF THE INVENTION

Since *homo sapiens* first began to walk upright, man has dealt with the pain, aggravation and loss of productivity arising from spinal injuries, particularly those to the lower back. It is not without good reason that the phrase, "Oh, my aching back!" is a common part of our everyday lexicon. The relative ease with which injuries to the spine and supporting musculature are incurred, as well as the debilitating effects of even slight injuries, merely adds to the overall severity of the problem of dealing with spinal injuries. Further aggravating the situation is that the most frequently prescribed regimen of treatment for spine-related injuries, short of surgical intervention, is the cessation or severe curtailment of almost all physical activities likely to give rise to torsional or compressional stresses to the affected regions of the spinal cord. In practical terms, due to the pervading effect of the spinal anatomy on all but the most sedentary and isolated of physical activities, almost complete immobility must be imposed to insure providing an injured spinal area sufficient opportunity to heal. In this context, the term "injury" relates not only to actual compression and torsional injuries to the various anatomical structures of the spinal cord and related neurophysiology, but also to general musculature strains of the large muscle groups interacting with various anatomical regions of the spinal cord.

The human spinal column is a major component of the skeletal system of thirty-three bones comprising seven cervical, twelve thoracic, and five lumbar vertebrae, with the latter merging endwardly into the five fused sacral and the four fused coccyx vertebrae. The twenty-four individual vertebrae have various bony projections with one projection, directed outward from the back of the spine, known as the spinous process. This spinous process of each vertebra can be felt along the back as hard knobs. The individual vertebrae are connected and supported by various cartilages, muscles and ligaments which allow flexibility for bending and twisting of the torso. Between each vertebra is an intervertebral disc which functions to cushion and separate each vertebra, helping to prevent compression of the peripheral spinal nerves branching off from the spinal cord and housed within the spinal column. When subject to extreme torsional stresses, the interior structure of the disk can rupture leading to a displacement of the intra-disk cushioning fluid and a resulting bulging of the outer disk surface. This bulging of the disk surface can impinge on nerve structures proximal to the disk area causing inflammation and further aggravation of the neurological anatomy involved. Such neurological involvement is invariably accompanied by pain, loss of strength in the lower extremities, or worse. In extreme cases, the outer surface of the disk can rupture completely leading to an extrusion of the viscous intra-disk fluid, a condition which generally requires invasive therapy.

Displacement of one or more of the individual vertebrae from its normal position can also create pressure against the spinal nerves, most often resulting in pain, frequently severe in intensity. Such displacement is often the result of unequal tension of the muscles supporting the spinal column, causing one or more of the individual vertebrae to be pulled out of alignment with the rest. This unequal tension of the muscles can be caused from a variety of factors, not all of which are physical. These include over-exertion, uneven muscular stress, emotional tension and direct physical trauma.

A significant proportion of back pain experienced by the general public occurs in the lower portion of the back generally referred to as the lumbar region, or spinal segments L-5 through L-1, specifically. In those instances where pain is the result of impingement of misaligned vertebral anatomy against spinal nerves, the pressure exerted against the nerves can be alleviated by re-aligning the affected vertebrae of this region, resulting in reduction or elimination of pain. In a similar fashion, a significant proportion of spinal injuries affecting the cervical region, or spinal segments C-1 through C-7, can also be alleviated through realignment of the affected vertebrae. A preferred clinical approach to achieve this realignment is through the use of procedures generally referred to as traction, which procedures shall be discussed at greater length below, in relation to the practice of the present invention. Additionally, for those injuries to the lumbar region arising from disk involvement, traction has also been demonstrated to be therapeutically effective in promoting healing of the affected anatomy with accompanying reduction in symptoms.

As a whole, back injuries are a very costly health problem for industry, as measured in terms of lost productivity. Some estimates place the total cost of back injuries to industry in the United States at approximately one hundred billion dollars per year. It is estimated that each year nearly half a million workers are permanently sidelined by back injuries. Lower back pain and other back injuries account for nearly forty percent of all work days missed, resulting in over 93 million lost work days per year. Many lower back injuries and much lower back pain result from improper lifting mechanics or techniques. Thus, many of these injuries that occur can be prevented by proper lifting techniques; however, even with training in proper techniques, many workers fail to use such techniques and become injured.

The lumbar spine can be injured in essentially two ways—namely, excessive compression or excessive torsion. If the former occurs, the most common result is a damaged vertebral endplate. The preferable remedy for such injury is rest, or a near-complete avoidance of any physical activity likely to place stress on the spinal column. Corrective surgery is rarely required, as is typical of the vast majority of day-to-day back injuries.

If excessive torsion or twisting occurs, the most common result is a damaged intervertebral disc. In extreme cases, the nucleus of an injured disc may rupture the annulus of the disc and protrude therethrough. Such a protruded disc, or "slipped disc" as it may colloquially be called, can pinch the spinal nerves causing extreme leg pain, or even paresis or paralysis. Corrective surgery to remove disc protrusions or even entire discs may be required. A series of relatively minor torsional injuries, if not allowed to heal, may result in a significantly weakened disc, which may be susceptible to more serious injury. The lumbar spine is generally more susceptible to injury by torsion than by compression. Continued twisting toward an injured side may aggravate the injury and significantly interfere with the healing process.

Because the human spine is the essential load bearing component in the human skeleton, an injury to any region of the spine almost inevitably causes at least some discomfort, immobility and/or pain. After an injury to the spine has occurred, it is critical that the spine be given an opportunity to heal itself. Spinal motion in the direction of the injury must be avoided if the injury is not to be aggravated, and given an opportunity to heal. If such opportunity is not provided, an injury may never heal or may become severely aggravated, causing increasing discomfort and incapacitation to the affected individual. However, because the spine is in constant everyday use, it is continuously subjected to stresses which may interfere with the healing process. In many instances, short of a significant period of absolute bed rest, or even more drastic, non-surgical measures such as epidural injections of anti-inflammatory agents into the spinal region, a spinal injury may never heal properly.

Due to the alarming frequency of spinal injuries, and the general economic impact on the productivity and efficiency of both industrial workers and the general populace that results from such conditions, considerable attention has been directed toward the development of devices designed to address the problems associated with back and neck pain of varying etiologies. In general, these devices can be characterized according to the following categories. First of all, there is a multitude of devices designed to prevent the occurrence of lower back injuries such as support belts and braces for workers engaged in repetitive lifting activities, or for the general populace during occasional lifting or athletic endeavors. Secondly, there are devices designed to be worn during everyday activities by individuals already exhibiting lumbar or cervical spinal injury symptoms. These devices, which can, in some cases involving the lumbar region, be similar in design to the preventative devices, allow the wearer to engage in activities while, in theory, still removing sufficient stress from the affected region of the spine to permit some limited healing of existing injuries, obviating the need for complete inactivity during the healing process. Lastly, there is a class of devices, generally of a far more complex scope mechanically, that are designed to provide active therapeutic benefit in a clinical setting to the injured user. Mechanical and/or gravitational traction devices for treating either the cervical or lumbar regions of the spine are exemplary of such devices.

With respect to the first class of devices mentioned above, it has been found that provision of additional support to the lower backs of workers through the use of belts, braces or wraps can considerably reduce the occurrence of back injuries, perhaps because such devices both provide added support, and encourage and remind workers to use better lifting technique. Such belts, braces or wraps appear to provide support by compressing the tissue around the spine so as to stabilize the lumbar region and prevent substantial lateral motion of the lumbar vertebrae relative to one another which, if left unconstrained, could otherwise occur and cause painful injury. Generally, such devices are of little benefit, for a variety of practical reasons, for prevention of injuries to the cervical region of the spine.

Many of the support belts used in the past were merely widened belts which were tightened to provide counter pressure, and did not promote correct extension of the spine. This type of device is exemplified by the U.S. Pat. No. 4,685,668, issued on a weight lifting belt to T. L. Newlin, Jr. on Aug. 11, 1987. These belts were relatively rigid and too much pressure could be applied directly on the spinous processes of the vertebrae, which was especially evident when the wearer bent over, resulting in pain along the spine. Wearing this type of belt for an extended period of time also tended to constrict blood flow and cause skin irritation.

Many of these prior art belts, braces or wraps have also been designed specifically to reinforce proper lifting techniques. When lifting heavy objects, it is preferable to use the legs as much as possible to perform the lift, thus relieving strain from the spine and muscles of the back. To insure that the legs are doing most of the lifting as opposed to the back, the lift should begin with the lifter in a squatting position with the back aligned within 45° of vertical. However, individuals often lift items with the back aligned 45°–90° beyond vertical such that the back bears most of the load during lifting. Many braces incorporate features which make it uncomfortable for a wearer to bend their back more than 45 degrees from vertical, thereby mechanically constraining the wearer from exceeding a degree of alignment of the back associated with proper lifting technique.

Often these devices employ padded regions designed to come in contact with the lumbar region of the spine, providing additional support to that region. Specific examples of belts designed to place various pads against the lumbar region of the wearer's back are shown in U.S. Pat. No. 4,991,573 to Miller in which the principal inventive focus of the device is the specific design of the lumbar pad; U.S. Pat. No. 5,188,586 to Castel et al. which discloses a back brace designed to prevent injuries to the lower back and impose proper liking technique on the wearer by constraining the range of motion during lifting; U.S. Pat. No. 4,768,499 to Kemp discloses a lifting belt with an unpadded lumbar panel, also designed to provide additional support to the abdominal region of the wearer during lifting; and U.S. Pat. No. 5,060,639 to Marcus which also discloses a back support providing additional support to the abdominal region of the wearer, including an embodiment suited for use by expectant mothers in the latter stages of pregnancy.

Numerous examples also exist of braces and belts which utilize a lumbar pad comprising fluid-filled compartments designed to conform to the unique contours of the wearer's back. For example, U.S. Pat. No. 4,622,957, which issued Nov. 18, 1986 to James D. Curlee, discloses a therapeutic corset adapted for the sacrum, lumbar and thoracic regions of the body. The corset includes a padded bladder provided with a duct for introducing fluid. The inflated bladder is disposed next to the user for the purpose of "filling" the unique contours of the sacro-lumbar region of the spine by providing a pressure for comfort to specific areas while controlling the overall stability of the thoracic spinal region. U.S. Pat. No. 4,552,135, which issued Nov. 12, 1985 to Gabor B. Racz, et al., also shows a "Lumbar Belt" with a relatively large rear belt section superimposed over the small of the back, and an air-filled chamber disposed between the small of the back and the belt. U.S. Pat. No. 5,111,807 to Spahn et al. also discloses a back belt with a pressurizable air chamber in the lumbar region pad, along with unique connector means designed to couple the diverse materials of construction of the belt in a manner superior to that of conventional sewing. However, all of these devices, although designed primarily to constrain the range of motion of the wearer to prevent injury, also result in a compression of the lumbar area which can have little or no therapeutic value and, in some instances, can actually result in an increase in the likelihood of the wearer to sustain a compressive-type injury.

In conformance with the second category of back devices described above, braces and belts of various designs are used to support the lumbar region of the spine after it has been injured. An example of such a device is disclosed in U.S. Pat. No. 4,691,696 to Farfan de los Godos which comprises a belt with one or more bracing structures designed to prevent torsional rotation of the wearer's back in the direction of an existing injury, thereby relieving stress from the injured area and providing an opportunity for the injury to heal.

Additional support braces exist in the prior art, such as that disclosed in U.S. Pat. No. 5,062,414 to Grim which utilize one or more fluid-filled chambers in the lumbar region of the belt, optionally in conjunction with electrically heated resistive elements designed to warm the injured area. Another example of a brace comprising fluid-filled bladders in a lumbar pad, along with electrically heated resistive elements, is disclosed in U.S. Pat. No. 4,702,235 to Hong. The Sports Plus II Belt, as shown in the AliMed catalog of 1995, on page S108, utilizes a plurality of vertically-oriented air-filled chambers that are distributed within the belt and extend beyond the lumbar region alone. However, these chambers are capable of expansion only in a radial direction and, thus, can serve only to tighten the belt circumferentially around the wearer's waist. Moreover, the Sports Plus II Belt has no horizontally disposed support members capable of transmitting vertically directed forces for relieving gravitational stresses on the lumbar region of the spine or creating a traction-like effect.

Additionally, there are several well known braces of the wrap-around corset type. Such corset braces wrap around the trunk of the body in the region of the lumbar spine. Such braces, however, are intended to reduce the compressive stress in the lumbar spine or to totally immobilize it. They are thus of limited value in the treatment of torsional or twisting injuries. In addition, they may be uncomfortable and difficult to fit to larger persons. Moreover, the highly constraining corset design imparts almost complete immobility to the torso of the wearer and is, therefore, ill-suited for use while pursuing day-to-day activities. Rigidly reinforced or rigid frame back braces are also well known. Such braces, however, also completely immobilize the entire spine. A patient using such a brace is rendered essentially disabled because he cannot move his spine in any way.

According to the third category of back devices described above, there are a number of braces and other such devices which are designed to provide active therapeutic benefit and to promote healing of the injured area. Generally, these devices can range from full-scale clinical appliances in the form of tables, chairs or other like structures, to belts and slings designed to be used in conjunction with large appliances. In theory, these devices function by suspending the weight of the affected patient in a manner that almost totally removes all gravitational stresses from the affected area of the spine. Thus, in contrast to the second category of devices described above, traction apparati do far more than merely constrain the movement of the affected region of the body. Generally, they are part of an aggressive, non-surgical or post-surgical regimen designed to keep the spine free from torsional and compressive forces, thus allowing the injured area to heal as rapidly and effectively as possible. The major drawback of most tractional therapies is that, due to the complexity of the apparatus and the need for substantial intervention by an appropriately trained health care professional to assure proper therapeutic use and optimal benefit, they are suited only for use in controlled, clinical settings. The time that a patient spends in a normal traction device must be dedicated time during which the patient is incapable of participating in any other activities.

An example of an orthopedic lumbar traction brace used in conjunction with traction appliances is disclosed in U.S. Pat. No. 4,269,179 to Burton et al. The brace of the Burton et al. patent is designed to be attached to the lower rib cage of the patient. The patient, while wearing the device, is suspended through the supporting straps of the device from a multiple-position table which can be adjusted to an optimal angle to achieve a desired amount of gravity traction. Thus, the weight of the patient's upper body is suspended from the brace about the patient's lower rib area and the lumbar region of the spine is relieved of the normal gravitational stresses the patient's body weight would impose even when completely motionless in a standing or sitting position. In conformity with the general comments above, a patient using the brace and traction device disclosed in the Burton et al. patent would be precluded from engaging in physical activity of almost any kind.

U.S. Pat. No. 4,991,572 to Chases discloses another type of lumbar traction harness designed in theory to use the principles of gravity traction to relieve stresses from the lumbar spinal region, permitting efficient healing of the affected area. Unlike the device of the Burton et al. patent, the Chases device utilizes an air-inflated bladder to increase the comfort of a patient using the device for traction therapy. This device is basically a traction sling which is adaptable to use in a variety of conformations and patient alignments. This variety of configurations is best illustrated by reference to FIGS. 6–11 of the Chases reference. As disclosed in the reference, the principal advantage of this device is its flexibility of use, being adaptable to a number of patient orientations, unlike the majority of prior art traction table devices, whether mechanical or gravitational, such as those used in conjunction with the device of the Burton et al. patent. However, as is universally true of this type of therapeutic traction device, the patient undergoing therapy must dedicate the time to participation in the therapy and cannot pursue any normal day-today activities, whether or not employment-related, during therapy.

Similarly, treatment of cervical injuries or disorders often requires cervical traction for treating trauma to the muscles and ligaments of the neck and the cervical and upper thoracic vertebrae and associated spinal nerves. By applying cervical traction, a "cervical separation" is produced which alleviates pain caused by compression on the nerves, while allowing more blood flow to the affected tissue that speeds the healing process.

Normally, in the early stages of applying traction, cervical traction forces are most easily controlled when the patient is confined to a hospital bed where more complex and expensive traction equipment is carefully controlled by medical professionals. When the patient has reached a point in the healing process where such a level of clinical treatment is not needed, other controlled traction devices may be prescribed and used by the patient.

One such home use traction device is an "over-door" cervical traction system in which traction forces are applied to a head halter or harness placed under the chin and occipital lobe areas. (See Flaghouse Rehab, Inc. Catalog, 1993, p. 64.) The harness is connected to a hanger that attaches to a door and holds a water-filled weight bag that applies a controlled amount of upward traction force on the harness by gravity while the patient sits next to the door that supports the hanger and weight bag. This traction system applies traction forces by the weight bag pulling the harness upwardly from below the chin region and the base of the skull. The amount of water contained in a weight bag controls the amount of traction force. Although this system is useful, it requires a patient to sit in one place for long periods of time.

Another prior art patient-controlled cervical traction device is available under the name Pronex from Glacier Cross, Inc. This device includes a U-shaped block that fits behind the patient's neck and rests on the patient's shoulders. An air-inflatable bellows in the middle of the block applies lateral lifting forces upwardly to pillows on opposite sides of the patient's neck. This device requires the patient to be immobilized in a horizontal position while traction is applied. The traction force is not uniform around the entire neck region and the bellows, being located at the middle of the device, can apply undesired inward pressure to the middle of the patient's neck and windpipe. Such a device is similar in function and design to that disclosed in U.S. Pat. No. 5,441,479 to Chitwood, issued Aug. 15, 1995.

U.S. Pat. No. 5,403,266 to Bragg et al., issued Apr. 4, 1995, discloses a cervical traction collar that can be used by a patient to apply a controlled amount of traction-type force to the cervical region. The device of this patent uses a circumferentially-distributed air-inflated bladder disposed at the bottom edge of a rigid central brace portion similar to conventional rigid cervical braces (see, for example, U.S. Pat. No. 5,230,698 to Garth, issued Jul. 27, 1993). As the bladder inflates, the rigid brace portion is forced upward to towards the wearer's chin, exerting tractional forces on the cervical spinal region. However, significant disadvantages remain for a design of this sort in that the inflation of the circumferentially-distributed bladder is inevitably accompanied by a radial constriction of the wearer's lower neck region. The rigid neck brace portion of the device can also be a source of some discomfort to the wearer, thus diminishing the likelihood that the device will be worn for a sufficiently long period of time to optimize its clinical benefits.

Thus, each of the categories of spinal braces and devices described above, although useful, exhibit considerable drawbacks and inefficiencies. The first category of devices, those designed to prevent injury and/or to encourage proper lifting technique, are hampered by a limited efficacy. Furthermore, such devices generally act by compressing the lumbar region in a plurality of dimensions and, aside from restricting motion within a safe range, can possibly lead to an increased likelihood of certain types of back injuries. The second category of devices, those designed to protect an injured wearer while the wearer engages in physical activities, offers not much more protection than those devices designed to decrease the likelihood of initial injury. These latter devices function merely by restricting motion and/or by providing direct support to the lumbar or cervical regions. Certain devices are also capable of providing heat to the affected area as well. However, both of these initial categories of devices, although they permit the wearer some range of physical activity, can do no more to treat existing injuries than to minimize the likelihood of re-injuring an affected area, or aggravating an existing injury. They are incapable of providing active therapeutic benefits leading to enhanced healing of injuries of the various spinal regions. Despite whatever other utility these devices may display, the inability to actively promote healing is a significant drawback to these types of devices.

The last category of devices, those exemplified by various designs of traction devices, offer the one significant advantage that the previous two types of devices are incapable of providing—active promotion of healing. However, even these devices suffer from a significant limitation. While undergoing therapy with these devices, the patient is totally incapable of pursuing any other type of physical activity. In this manner, although some productivity gains could be realized through optimizing the healing process and, consequently, minimizing the time away from work and other productive endeavors, the time spent in traction therapy is time that is unavailable for productive activity. Accordingly, any device that is adaptable to everyday use and permits the wearer to pursue day-to-day activities, yet also provides some protection to the spine as it is healing, would be advantageous. Even more advantageous would be a device that would not only protect the injured spine, allowing it to heal, but also could provide active therapeutic benefit to the patient, while still allowing the patient to pursue a reasonably full, everyday life. Until the disclosure contained herein of the present invention, this has been impossible to achieve through use of the prior art devices. Now, the present invention provides an inflatable spinal brace that is suitable for everyday use; provides protection against injury and aggravation of existing injury; and provides the type of active therapeutic benefit in the healing of spine-related injuries that was previously possible only through full scale clinical appliances. All of this, as well as additional benefits, will be apparent from the detailed description of the invention provided below.

BRIEF DESCRIPTION OF THE DRAWINGS

FIG. 3 provided in two panels, illustrates the relationship of the anatomy of the ribs to the spine: panel A is a lateral view of ribs and spine; panel B is a partial sectional view of the skeletal anatomy of the ribs and spine, taken along line 3—3 of FIG. 3A.

DETAILED DESCRIPTION OF PREFERRED

Figure 1:
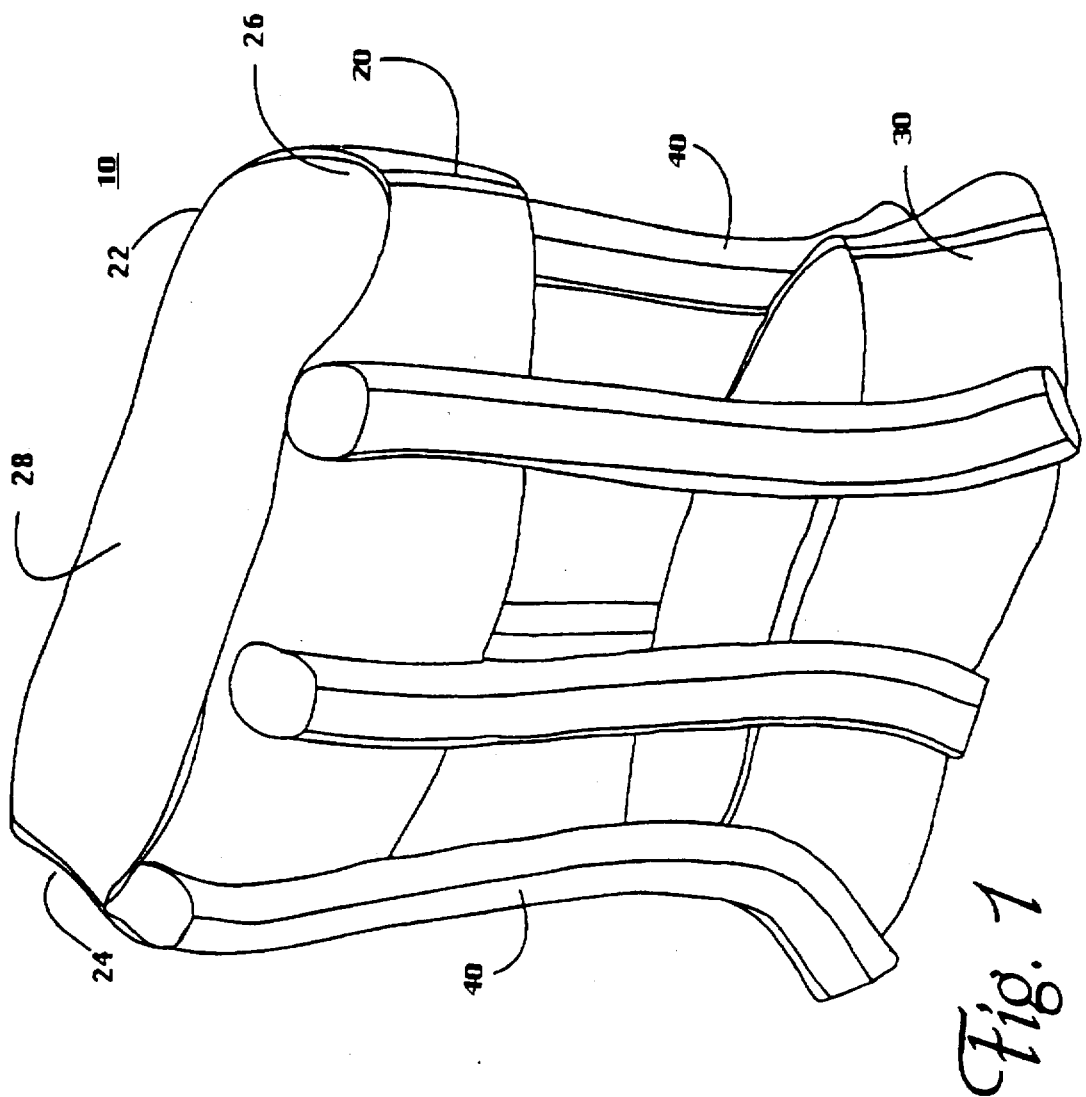
FIG. 1 provides a generalized perspective illustration of an embodiment of the inflatable traction device of the invention.

Referring now to FIG. 1, there is depicted at 10 a generalized perspective illustration of a first embodiment of the inflatable traction device of the invention, presented with a level of detail sufficient to inform the skilled practitioner of the concept and the practice of the invention. The embodiment illustrated in FIG. 1 is adapted for use as a lumbar traction vest. As can be seen in FIG. 1, the traction vest of the invention 10 is comprised of an upper horizontal support member 20, a lower horizontal support, or belt, member 30, and a plurality of individual, vertically-inflatable support members 40.

As depicted in FIG. 1, the embodiment of the present invention provides a generalized level of detail. The upper horizontal support member 20 is depicted as a unit of one-piece construction. In practice, there are a variety of constructions that are functional for the upper horizontal support member 20. To one of ordinary skill in the appropriate area of art, it will be apparent that the choice of which of these various methods of construction are utilized to prepare an embodiment of the present invention will be determined by such factors as available materials, cost, durability, comfort, and the like. Perhaps the simplest method of construction for the upper torso member 20 would be to utilize an elasticized material such as would be used in the fabrication of support undergarments.

As is depicted in FIG. 1, the upper horizontal support member has a top edge 22. The contour followed by the top edge 22 is designed to allow the arms of the wearer to extend comfortably above the upper member 20. Toward this end, the upper horizontal support member has a right arm access contour 24, and a left arm access contour 26. If a one-piece unitary construction is utilized for the upper horizontal support member 20, then it is anticipated that the lumbar traction vest of the present embodiment of the invention would be donned by the wearer by first slipping the arms and head through the upper support member 20.

A key consideration to weigh in the selection of design materials and in the actual construction of the upper member would be the ultimate comfort of the wearer. This comfort would depend to a large extent on the degree of flexibility of the material of construction of the upper horizontal support member 20, as well as the size of the wearer and the actual fabric of construction. It will be recognized that certain materials of construction, such as certain kinds of plastic and the like, would have lower degrees of flexibility and also could prove to be uncomfortable to the wearer in that they would make it difficult for circulation of air between the inside surface 28 of the upper member, and the outer surface of the wearer. Of additional consideration in this regard would be the ability of the material of construction to "breath" sufficiently to allow the passage of moisture from the skin of the wearer to the atmosphere. With this in mind, materials such as plastics would be less suitable than the type of flexible fabric material normally associated with elasticized support undergarments.

Alternatively, as would be recognized by one of skill in the art, a variety of other designs could be used for the construction of the upper member. The upper support member 20 could be constructed of a semi-flexible material, or even a canvas or nylon of sufficient strength, with an opening disposed either to the front, to the rear, or to either side of the torso, wherein the opening may be secured by adjustable means such as laces, buckles, or Velcro™-type hook and loop closures. With a construction requiring closure in such fashion, the wearer could don the vest in a simpler manner, one that is similar to donning a regular garment. Construction of the upper support member 20 requiring closure in this manner would also provide additional means to adjust the fit of the vest to the wearer, if necessary. As will be apparent from the description below, the fit of the upper member can be critical in that it is an essential element in the transfer of gravitational forces to the proper structural elements of the vest of the present embodiment.

The lower horizontal support, or belt, member 30 is depicted in FIG. 1 in a single unitary construction. Although it is theoretically possible, utilizing materials of sufficient flexibility and stretch, to so construct the lower horizontal member, preferably it is advisable to construct the lower member along the lines of a conventional front-buckling belt for the embodiment depicted in FIG. 1. Once again, both the specifics of construction, as well as the material choices, for the lower horizontal member 30 depend upon a number of practical factors, such as availability, comfort, cost, and the like. It is contemplated that the lower support or belt member 30 can most practically be constructed from readily available weight-supporting belts such as those utilized in conjunction with external frame backpacks.

As used with those devices, these types of belts are designed to distribute the bulk of the gravitational forces exerted through the entire apparatus to a portion of the wearer's body, namely the hips, that is best suited to bear that load. These types of belts are typically worn fairly low on the hips and are tightened snugly thereto to ensure that the distribution of forces is accomplished in an efficient and effective manner. In a like fashion, the lower horizontal support member 30 of the lumbar traction vest 10 is designed to receive the bulk of the weight-related forces acting on the vest 10, and transfer those forces to the wearer's hips. It should be recognized here that the phenomenon that occurs through this weight transfer mechanism is essentially the same phenomenon that produces the therapeutic effect of large traction appliances used in clinical settings. In the practice of the present invention, the weight of the upper body of the wearer is essentially hung from the upper torso member 20, and distributed through the inflatable support members 40 to the lower belt member 30. Thus, the weight forces normally experienced by the spinal region affected by this or any other embodiment of the present invention are instead carried by anatomical structures, such as the hips of the wearer for the lumbar vest, best suited for carrying such a load, leaving the vertebrae of the affected spinal region free from compressional and torsional stress and, therefore, allowing injured spinal anatomy a chance to heal properly. Once again, this is the same basic concept that is in operation in the use of full-sized mechanical traction appliances such as those of the prior art discussed above.

Figure 2:
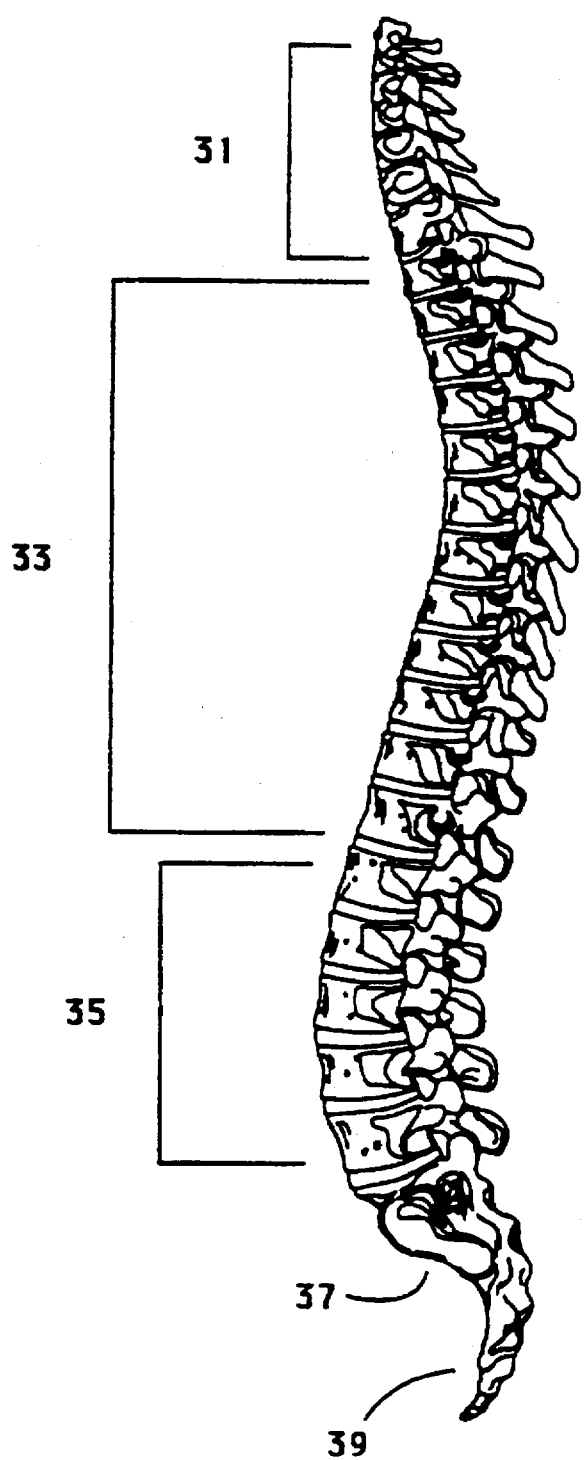
FIG. 2 provides a lateral view of the human spine, illustrating the various spinal regions: the cervical, the thoracic, the lumbar, the sacral and the coccyx.

As has been demonstrated through the use of large-scale gravitational traction devices, the mechanical transfer of gravitational forces necessary to produce the desired traction effect, where these forces are removed or significantly reduced from the lumbar region of the spine, is achieved through the leveraging of skeletal structures associated with the upper spinal region. By reference to FIG. 2, and in accord with the discussion above, there is illustrated a lateral view of the human spine comprising thirty-three bones—seven of the cervical region 31, twelve of the thoracic region 33, and the five of the lumbar vertebrae 35, with the latter merging endwardly into the five fused sacral 37, and the four fused coccyx vertebrae 39. The relationship between the various spinal regions and the ribs is illustrated in FIG. 3 where, in panel A, there is illustrated a lateral view of the ribs, along with the associated spinal regions, primarily the thoracic 33. In FIG. 3B, there is illustrated a partial sectional view of the skeletal anatomy of the ribs and spine, taken along line 3—3 of FIG. 3A. As these figures illustrate, the ribs, including the lowest "false" ribs, are integral with the twelve thoracic vertebrae.

In the practice of the present invention, the upper horizontal support member 20 effectively grasps the ribs primarily, although not exclusively, along the lower region. This "grabbing" of the ribs is the initial step in the mechanical transfer of forces away from the lumbar region of the spine. In this fashion, the ribs, "grabbed" by the upper horizontal support member, act as a lever to transfer the applied forces to and from the upper spinal region, most probably the T1 to T5 vertebrae and associated rib structure. The vertically oriented inflatable support members 40 form the next link in the mechanical chain through which forces are removed from the lumbar region of the spine. Ultimately, through the inflatable support members 40, the forces that are normally borne by the lumbar vertebrae 35 and associated disk anatomy are transferred to the lower horizontal member 30 and onto the wearer's hips.

In light of the "mechanics" by which the device of this embodiment of the present invention functions, it should be apparent to one of skill in the art that the structure of the upper horizontal support member 20 must meet the relatively simple criterion of being able to effectively and firmly grasp the rib cage so as to use the ribs to lever the applied forces to and from the upper thoracic vertebrae. In light of this criterion, a wide range of structural arrangements for the upper support member 20 are possible. The principal benefit of this design flexibility is that the device of the invention is capable of being fabricated in a lightweight and comfortable form, appropriate for ambulatory use over extended periods of time. As important, the construction of the lumbar traction vest 10 of the above-described embodiment is such that the vest possesses sufficient flexibility to allow the wearer to engage in a reasonable range of physical activity, all without imparting undue stress to the injured spinal region. This same principle is in operation, although to a less noticeable extent, for embodiments of the invention designed to affect the cervical region of the spine.

As discussed immediately above, key elements in accomplishing the transfer of forces in the traction vest embodiment to the lower support member, while at the same time maintaining flexibility of the vest that permits the wearer to engage in moderate levels of physical activity, are the vertical inflatable support members 40. As illustrated in FIG. 1, the inflatable lumbar traction vest 10 of the instant embodiment is shown with five vertical inflatable support members 40. Although the exact number of support members 40 incorporated into the design of the traction vest 10 is important, it is not critical to achieving the desired function of the vest that there specifically be five vertical members. The inventor considers five vertical members to be an ideal, although not essential, configuration. Such a number of support members 40 provides sufficient support between the upper and lower members of the vest, as well as allowing for sufficient flexibility to permit the wearer a reasonable range of activities while wearing the vest.

In determining an optimal number of support members for a particular embodiment of the present invention, the most critical factor is the total amount of force which the device must be able to apply to the affected region of the spine. In the embodiment described above for a traction vest designed to affect the lumber region of the spine, the most practical starting point for determining the force that needs to be applied, and from that the optimal number of vertical support members, is a direct comparison to the type of traction appliances referred to above with respect to the discussion of U.S. Pat. No. 4,269,179 to Burton et al. In a Burton-type traction device, the maximum amount of force that could be applied to a patient's lumbar spinal region would be equal to approximately 40–50% of that patient's body weight. This would represent an upper boundary for such a range of forces, in that to achieve that amount of force through a traction device, the inclined table on which the patient would be suspended would have to be at a maximum angle of inclination approaching the vertical. In such an extreme position, the patient's weight from the lower half of the body would be suspended from the traction device. Thus, for a 200-lb. man, the maximum expected force to be applied to the lumbar region through the gravitational traction device would be approximately 80–100 lbs.

In any embodiment of the present invention, the maximum amount of force exerted on the affected spinal region through a vertical support member of the device would be a function of the gas pressure within the inflatable member and the horizontal cross-section of the support member. If we assume for sake of simplicity that the vertical support member is in a cylindrical configuration and that the horizontal cross-section of the member is simply the area of the end of the cylinder, then the force exerted by that support member can be described by the following equation:

$$F = P \pi r^2 \quad (1)$$

where F is the force, P is the inflation pressure of the support member, r is the radius of the cylindrical support member, and $\pi$ is the familiar mathematical constant. Where there is a plurality of vertical support members for an embodiment of the present invention, then the total force, $F_{tot}$, exerted on the affected spinal region through the traction device will be simply the sum of the forces exerted through each of the support members. For n vertical support members, each of radius $r_n$, then Eq. (1) can be expressed as follows:

$$F_{tot} = (P_1 \pi r_1^2) + (P_2 \pi r_2^2) + (P_n \pi r_n^2) \quad (2)$$

For the expected situation where all of the vertical support members are of the same radius (r) and inflated to the same gas pressure (P), then Eq. (2) can be simplified to the following expression:

$$F_{tot} = nP\pi r^2 \quad (3)$$

where n is the number of inflatable vertical support members. Thus, using Eq. (3), it is possible to determine the optimal number of support members to achieve a desired total force at a specific target inflation pressure and radius. Of course, other calculations are possible using Eq. (3), depending on the particular variable being optimized and the other information available.

Thus, it will be recognized by one of appropriate skill that the actual number of vertical support members 40 can be fewer than five, or more than five. Generally speaking, it would be undesirable for the number of inflatable support members to be less than four. With a configuration of four vertical support members, these would preferably be distributed with two in the front of the vest and two in the rear of the vest. It is also possible to have more than five members, such as six, where the plurality of vertical inflatable support members 40 would be distributed equally between the front and back portions of the vest 10. It is also contemplated that a greater number of vertical support members 40 may be desirable for some applications where greater levels of constraint of movement may be preferable, such as those designed to correct deviations in spinal conformation typical of conditions such as scoliosis, lordosis or kyphosis.

There also exists a practical limit on the upper number of vertical support members 40 used in the vest. A significant, advantageous feature of the vertical orientation of the inflatable support members of the invention lies in the fact that such an orientation leads directly to the mechanical distribution of forces vertically within the vest 10. This is achieved through a vertical distribution forces through the inflatable support members that effectively results in the suspension of a major proportion of the wearer's body weight from the upper horizontal support member which weight, in turn, is transferred to and supported by the lower horizontal support member or belt, in the case of the traction vest embodiment. Alternative orientations of inflatable members, for example in a horizontal orientation or in a torroidal configuration, could lead directly to spinal compression, as opposed to spinal support or re-distribution of forces acting on the spine. Thus, inflation of a horizontally-oriented bladder system could result in the same type of effect evidenced with prior art corset-type braces discussed above which can significantly immobilize the wearer. It is contemplated that a similar effect could result from the use of too many vertical inflatable members in the design of the vest of the present invention.

Figure 4:
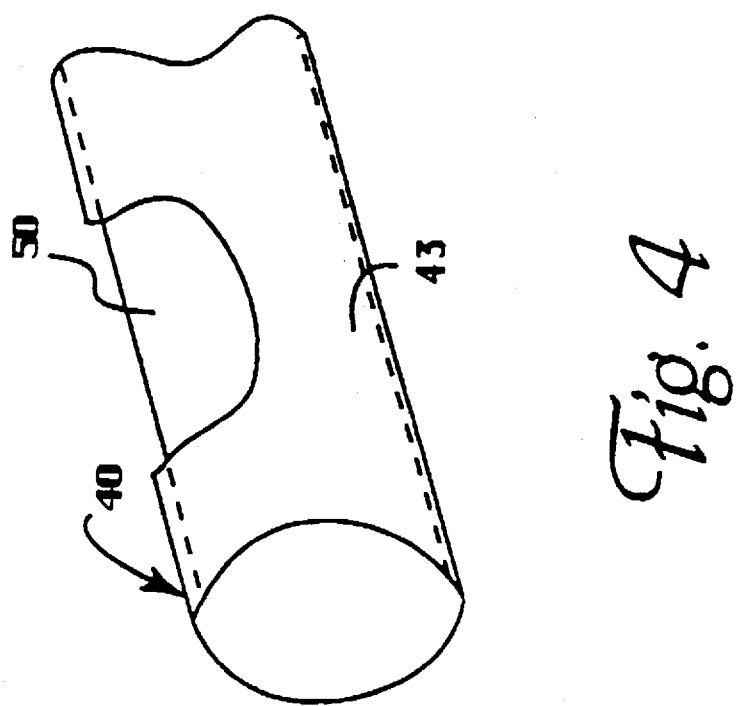
FIG. 4 illustrates a partial cut-out perspective view of the vertical support members of the invention.
Figure 5:
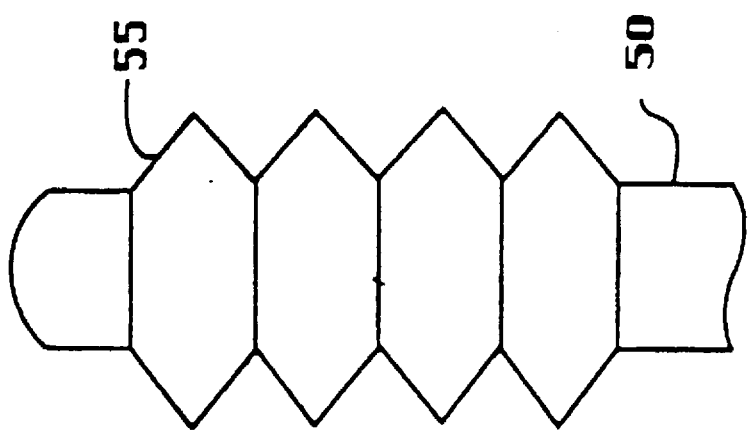
FIG. 5 is an illustration of an air-inflatable bladder of the present invention incorporating a vertically expanding bellows portion.

As shown in FIG. 1, the plurality of vertical support members 40 are of approximately equal diameter, which diameter is approximately 1 inch or more, although individual members may have a slightly different conformation depending upon their relative positions on the vest 10. Essential to the effective function of these vertical support members are the air-inflatable bladders 50, as illustrated in FIG. 4 in partial cut-away section. The embodiment of the present invention illustrated in FIG. 4 contemplates but a single inflatable bladder 50 present in each of the vertical support members 40. However, it will be recognized that it is possible for a plurality of essentially cylindrical bladders to be utilized in each vertical support member 40, each of the plurality in fluid communication so that a single source of air or other suitable gas would be capable of inflating the plurality of bladders 50 in a single vertical support member 40. It is also contemplated, as illustrated in FIG. 5, that the bladders can be constructed of a bellows design to further aid in the upward vertical expansion, and subsequent vertical distribution of forces, of the support members 40. As shown in FIG. 5, the individual bladders may be advantageously constructed with at least one bellows portion 55, although it is possible to construct any one bladder 50 with a plurality of such bellows portions.

The bladders 50 may be constructed of a variety of materials possessing the desirable characteristics of flexibility and strength. However, it is contemplated that the preferable material of construction of the bladders 50 be latex due to the ease of fabrication possible with such material. Such material can be fabricated into appropriate bladders by specialty manufacturers such as North American Latex of Sullivan, Ind. As contemplated by this embodiment of the present invention, the diameter of the bladders 50 controls the diameter of the inflatable support members 40. Given the use of latex as the material of the bladders, a maximum practical diameter of the cylindrically-shaped bladders would be about 1 inch. Latex bladders of this diameter would be safely capable of inflation to a maximum pressure of approximately 20 lbs/in$^2$. However, it is necessary to inflate the bladders 50 only to a pressure in the range of 6–12 lbs/in$^2$ (see Eq. (3)) to achieve the desired mechanical characteristics of the vertical support members, at least for the majority of contemplated applications of the lumbar traction vest embodiment. Variation in the range of inflation pressure can also be achieved through selection of the material of construction of the bladders, as well as the number of vertical support members 40 utilized on the vest, and the number of bladder segments within any one support member 40. In the context of inflation pressure, it is important to remember that it is desired to retain a sufficient degree of flexibility in the fully inflated vest so that the wearer will not be so constrained in movement as to be practically immobile. For the majority of applications contemplated for the vest 10, it will remain preferable for the wearer to be free to engage in a reasonable degree of physical movement while wearing the vest. This is where selection of the material of construction of the bladders 50 becomes important; latex is particularly advantageous in that it is capable of maintaining sufficient flexibility when inflated to the desired level of pressure.

An additional consideration in the inflation of the vertical support members 40 is that it is preferable to have a mechanical means for constraining the radial expansion of the bladders during inflation. As explained at some length above, the traction effect of the device of the invention is achieved through vertical distribution of forces through the support members. To the extent that the inflatable bladders also expand radially (horizontally), no benefit is derived for the practice of the invention. The means for constraining radial inflation could be the outer portion 43 of the vertical support members 40. It could also be provided by a sheath surrounding the bladders 50, where the sheath is fabricated of a sufficiently stiff material. It is also possible that the walls of the bladders themselves could be integrally constructed with a material capable of vertical but not horizontal expansion upon inflation.

Depending upon the choice of material of construction for both the bladder and the outer portion 43 of the vertical support members, it may be necessary to incorporate additional support means into the bladders and/or the vertical support members. These additional support means serve the purpose of importing additional stiffness, and therefore support, to the vertical support means. Suitable material of construction for these additional support means may be wood, plastic or even metal. In the case of plastic, the individual additional support means may then be advantageously fabricated to a contour that matches the wearer's body contours. It is also possible to fabricate individual bladders 50 incorporating support means in the form of a flexible fabric material integrally constructed with the walls of the bladder.

Alternatively, for an application where it is desirable for the inflatable vest of the present invention to impose mechanical restraints on anatomical structures of the wearer's spinal region, as would be the case where the vest was utilized to import a construction to a mis-aligned spine typical of conditions such as scoliosis, lordosis or kyphosis, the additional support means may be constructed of a less flexible, stiffer material, preferably pre-molded to a desired conformation, An additional consideration in the function of the vertical support members is the material of construction of the outer portion 43 of the members 40. The specific material of construction chosen here is less critical than the choice of bladder material and will typically be driven by cost, availability and, to a lesser extent, comfort. It is possible for the outer portion of the vertical members to be constructed from such materials as canvas or nylon, although nylon would be preferable due to weight considerations. An additional function of the outer portion 43 of the vertical members 40, as mentioned above, is to constrain the inflation of the bladders 50 and to physically limit the expansion of the flexible bladders in a radial direction upon inflation, making possible the vertical distribution of forces.

Figure 6:
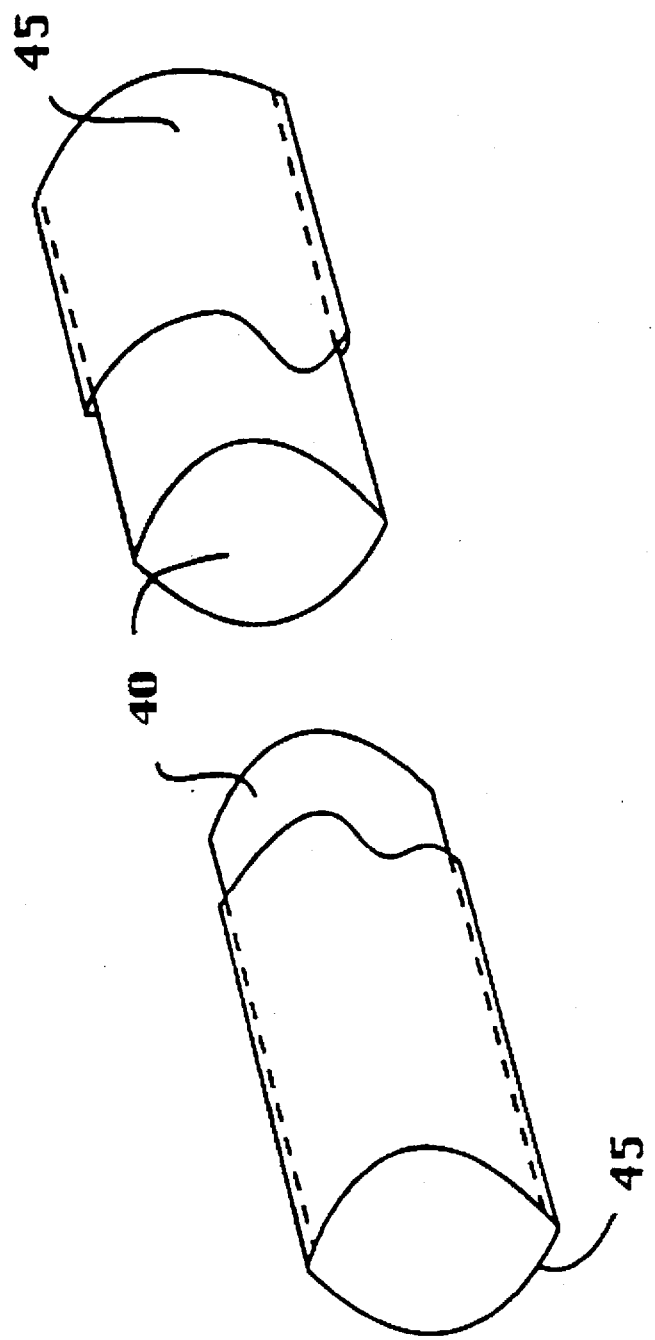
FIG. 6 provides an illustration of the vertical support members of the device of the invention further illustrating the receiving cup members affixed to the upper and lower horizontal support members of the vest.

The vertical support members 40 can be mechanically affixed to the upper support member 20 and the lower member by a variety of means. As illustrated in FIG. 6, each end of the vertical support members is placed in receiving cup members 45 permanently affixed to the vertical members of the vest by a variety of means, such as gluing, sewing, and the like. It is also contemplated that the vertical support members can be directly coupled to the horizontal members of the vest 20 without the use of receiving cup members. It is also contemplated that the overall design of the vest embodiment be more unitary than is apparent from the depiction in FIG. 1. Thus, it may be advantageous to incorporate means for affixing vertical support means to the upper and lower horizontal support members integrally into a one-piece design which would provide an appearance that more closely resembles a typical vest worn as clothing. This would provide additional advantages in that the overall aesthetic appeal of the device would be enhanced. Since it is envisioned that the device of the present invention would be capable of being worn for extended periods of time, such considerations may be of some significance in a practical context. However, there are a variety of engineering and manufacturing considerations that will dictate the overall design of the vest, as well as the specific means of coupling the vertical support members 40 to the upper torso member 20 and the lower belt member 30. Such choices should be well within the experience of a practitioner of appropriate level of skill in the art. It should be noted that a primary consideration in the overall design of the upper and lower horizontal support members and how they interact mechanically with the vertical support members is that there must be a mechanical coupling between these structural elements so that the vertical forces generated by the expansion of the bladders 50 are in turn transmitted to the upper and lower horizontal members to achieve the desired traction effect.

Figure 7:
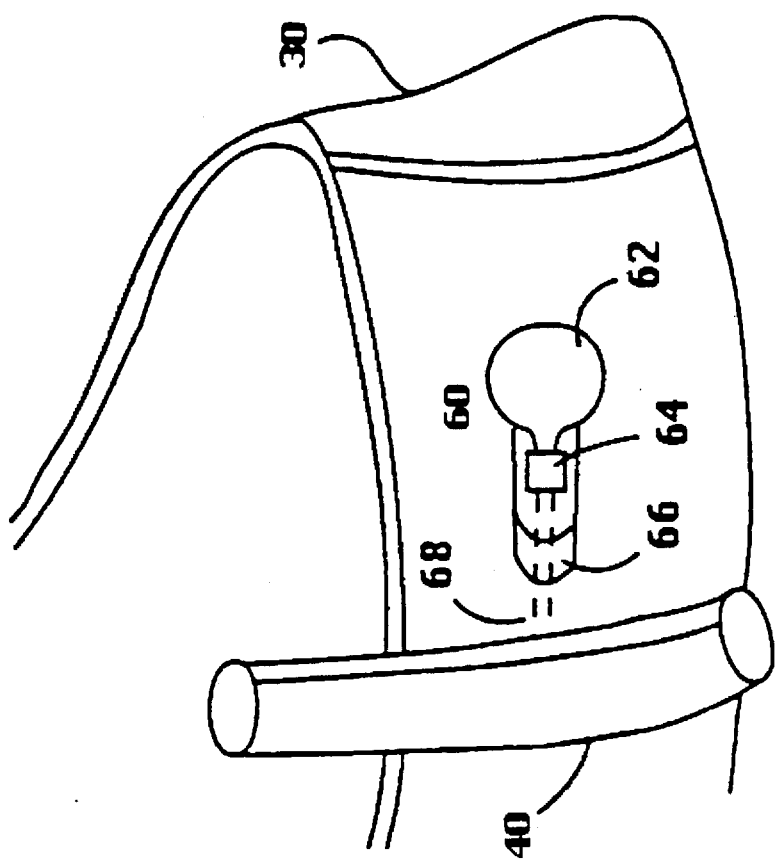
FIG. 7 provides, in perspective, an illustration of inflation means for the vest of the invention.

Inflation of the bladders 50 disposed inside the vertical support members may be accomplished by a variety of means, as would be apparent to a skilled practitioner. One of these is illustrated in FIG. 7. Illustrated therein is a hand pump mechanism shown generally at 60. This pump mechanism 60 comprises a removable pumping bulb 62, a pressure fitting 64, and a bladder access port 66. The bladder access port is, in turn, in fluid communication with a bladder channel 68 through which air is forced by hand squeezing of the pumping bulb 62. Such pressure fitting could be a common Schraeder-type valve typically found on bicycle and car tires. With such a fitting, pressure inside the bladders could be relieved through the simple act of depressing the central valve stem in the fitting. Alternatively, a Velcro™-type hook and loop closure (not shown) could be provided to cover the non-removable components of the inflation mechanism 60 when not in use.

It is contemplated that each of a plurality of inflation mechanisms 60 be in fluid communication with each of a plurality of bladders distributed throughout the vertical support members. In this fashion, it would be possible to selectively tailor the inflation pressure within the device to provide lesser pressure in some regions of the device, and greater pressure in others. It is contemplated that this type of custom adjustment of the inflatable bladder system of the device of the invention could be achieved to result in whatever degree of motion would be desired for a particular activity contemplated for the wearer. The number and distribution of such separate bladders within the bladder system of the vest would be limited by such practical considerations as the complexity of manufacture, the resulting costs of multiple-component systems, and the specific applications of the device. In addition, it is contemplated that and additional bladder, preferably in fluid communication with one or more of the vertically-oriented bladders, be placed so as to conform to the unique geometry of the lumbar curvature of the wearer's back.

Figure 8:
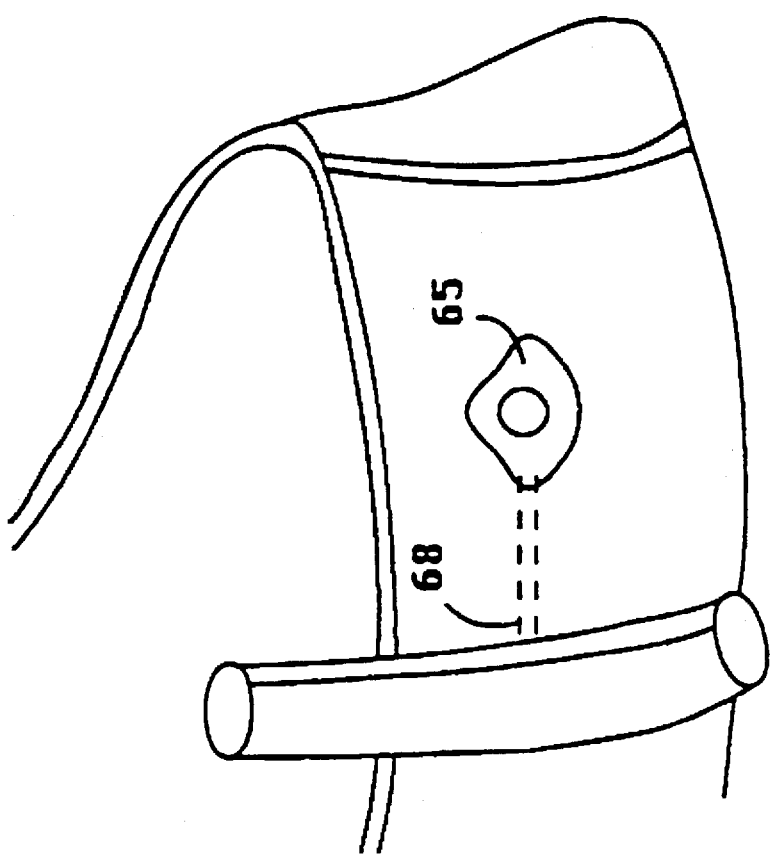
FIG. 8 provides an illustration of an alternative embodiment of the inflation means of the present invention.

It is also contemplated that alternative mechanisms be utilized for pressurizing the bladder system of the device. One of these is illustrated in FIG. 8. The mechanism contemplated here is a completely enclosed pump means 65 which is activated by downward pressure of the wearer's thumb on the convex surface of the pump means. Such systems find frequent use in inflatable sporting apparati. Usually associated with such inflation means are hand-operated pressure release valves (not shown) so that the air pressure within the bladders 50 may be relieved to facilitate the removal of the vest 10 from the wearer.

An alternative means for inflation of the bladder system within the vest is possible in conjunction with an important anticipated application of the lumbar traction vest embodiment of the invention. Currently, long-haul truck drivers are frequently beset with a variety of lower back ailments stemming from the repetitive bouncing and jarring such drivers experience during long hours of driving. Such conditions are often aggravated by the fact that these drivers frequently must go directly from long hours of driving, with accompanying stresses applied to the lower spinal regions, to unloading of the transported goods from their trucks at a given destination. If such lifting is not preceded by appropriate stretching of the lower back regions and warming up of the muscles involved in heavy lifting, then the chances of injury to the lower back become much higher. If the driver does not follow proper lifting technique, then the situation is exacerbated. The vest of this embodiment of the present invention provides an ideal means for such long-haul drivers to avoid injury to their lower backs, as well as aggravation of existing injuries during long hours behind the wheel. A significant advantage of the lumbar vest embodiment of the present invention, as described above, is that it is capable of being worn during a wide range of physical activity. Furthermore, it is comfortable enough to be worn for relatively long periods of time so that, even if the degree of therapeutic effect does not rise to the level associated with clinical traction appliances, the overall effect of the use of the vest embodiment of the invention can match or exceed that of the large appliances. Such characteristics make the vest of the present invention ideally suited for use by long haul truckers.

Most large tractor/trailer combinations employ a compressed air apparatus associated with the brake system of the truck. It is relatively easy to utilize a means to tap into that source of pressurized air and extend a hose and coupling means into the cabin of the truck for inflation of the bladders of the vest while the wearer is driving the truck. Connection to the compressed air system of the truck can be achieved by mechanical hose coupling devices such as a luer lock fitting. Thus, the wearer can inflate the vest while driving to a level of pressure that is personally comfortable, arrive at the scheduled destination, further adjust the inflation level using the air hose means, and then immediately upon parking the truck, begin to unload cargo while still wearing the vest of the invention, and after uncoupling from the air hose means. The embodiments of the present invention disclosed herein are uniquely capable due to their light weight and flexibility to meet various federal and state drivers' safety requirements for devices worn while operating commercial vehicles in the transport of goods in commerce.

Regardless of what mechanical means is used to bring pressurizing gases to the bladder system of the vest, the present invention contemplates the use of a check valve associated with each separate gas flow/bladder system within the vest so that there is no chance of an over-inflation occurring during wearing of the vest. Valves of this nature are well-known in the art. Typically, such valves can be selected or set to match the maximum rated inflation pressures of the individual bladders. Thus, when the pressure rises to the safe limit of a bladder, either during inflation or during use, the check valve will activate to relieve the buildup of pressure before damage can occur to the vest, or injury to the wearer.

Figure 9:
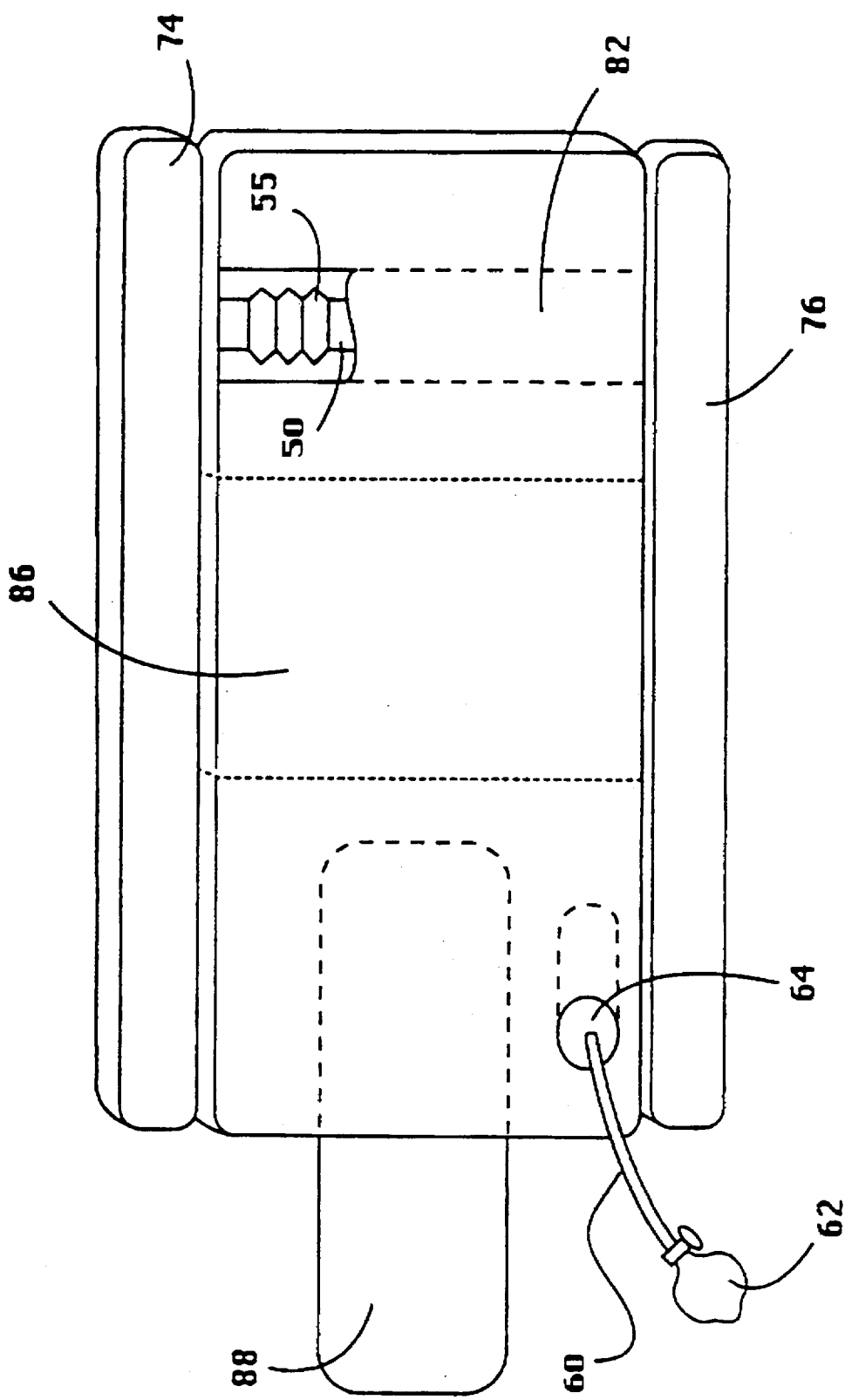
FIG. 9 provides an illustration of an alternative embodiment of the present invention, a cervical traction brace.

FIG. 9 illustrates an alternative embodiment of the present invention, shown generally at 70, designed to affect the cervical region of the spine. As depicted in FIG. 9, the cervical brace 70 is shown in a generalized, almost schematic, fashion designed to illustrate the main elements of the brace on a level of gross detail. FIG. 9 illustrates that the cervical brace 70 is comprised of at least three major components, an upper mandible support member 74, a lower clavicle support member 76, and a central bladder-containing portion 78. Disposed within the central bladder-containing portion 78 are a plurality of individual, vertically-inflating bladders 50, shown in FIG. 9, in partial cutaway view, with an optional bellows portion 55. The number and diameter of such bladders 55 can be calculated in accord with Eq. (3) above, as was described previously with the lumbar vest embodiment of the present invention. The exact construction of the central bladder-containing portion 78 of the present embodiment is subject, as with the previous embodiment, to substantial variability, as will be recognized by one of skill in the appropriate art. It is contemplated that the central portion 78 be constructed of a flexible fabric material onto which are affixed separate chambers within which are contained each of the plurality of bladders 50. It is also contemplated, by way of example only and without limitation, that the central portion 78 may be constructed of a foam material from which are excised suitable volumes for containing the vertically-expanding bladders 50.

As illustrated in FIG. 9, the central bladder-containing portion 78 of the cervical brace 70 also comprises a support region 86 disposed to be oriented to the back of the wearer's neck and designed to provide sufficient support in a front-to-back plane so as to restrict the range of motion to the rear of the wearer's head. Also shown in FIG. 9 is a means 88 for adjustably fastening the cervical brace 70 around a wearer's neck. FIG. 9, in addition, illustrates a pumping mechanism 60 through which the bladder system within the cervical brace 70 is inflated to a target pressure. Based upon analogy to existing mechanical traction devices, an optimal force to be achieved for cervical traction through use of this embodiment of the present invention would be approximately 15-25 pounds. Such an inflation mechanism comprises similarly-numbered elements as that for the mechanism of the embodiment of FIG. 7.

FIG. 9 illustrates the upper and lower support members of the cervical brace 70 at a gross level of detail only. It is contemplated that each of the horizontally disposed support members of the brace comprise additional detail, as would be appreciated by a skilled practitioner. For example, the upper or mandible support member may be contoured to fit the anatomical details of the wearer's chin and jaw area in order to attain a more effective fit of the brace to the individual wearer. It is contemplated that the upper support member 74 will be fabricated preferably of a relatively dense plastic foam in order to both provide support and resistance to the vertically-directed forces acting through the brace, at the same time as providing comfort to the wearer. Optionally, it is contemplated that the upper support member 74 may be covered with a comfortable, breathable fabric because it will be in direct contact with the wearer's skin for a segment of the support member's length.

The lower or clavicle support member 76 is also illustrated in FIG. 9 at a level of gross detail only. It is contemplated that this portion of the cervical traction brace 70 may assume a plurality of embodiments. In one embodiment, it may be constructed in a similar manner and of a similar material as the upper support member 74. Alternatively, it may also comprise an air-inflatable bladder, either with separate inflation means, or in direct fluid contact with the bladder system of the central bladder-containing portion 78. Regardless of the actual manner of construction selected for either of the two horizontally directed support members of the cervical brace 70, they must be designed so as to be able to withstand, and transmit where appropriate, the traction forces acting vertically through the brace. Although constructed on a smaller scale than the lumbar traction vest embodiment described above, the inflatable cervical traction brace of FIG. 9 functions on identical principles to those described for the previous embodiment. As the bladders are inflated, they expand vertically, exerting traction forces on the cervical region of the wearer's spine. The weight of the wearer's head is supported by the upper or mandible support member 74 and transmitted through the central bladder-containing portion 78 to the lower or clavicle support member. Thus, the gravitational forces acting on the wearer's cervical spinal region are relieved and actually borne by the wearer's upper chest and shoulder area, depending on the specific design of the lower support member. The end result is essentially identical to that obtained with the type of mechanical cervical traction devices described in the Background of the invention section, supra. The advantage, therefore, of the present invention is that the therapeutic gains to be realized from traction treatment can be achieved without resort to immobilizing the patient, with a resultant loss of productive time.

Although the above description of preferred embodiments of the present invention clearly illustrates the concepts and practice of the invention, it will be recognized by one of skill in the art that the present invention may assume a plurality of embodiments. In recognition of this, the description provided above is illustrative only and not intruded as a limitation of what the applicant considers to be his invention, which invention is limited only by the metes and bounds of the claims set forth below.

What is claimed is:

1. An ambulatory spinal traction device for applying primarily vertically directed forces to an anatomical region of a human spine wherein the device comprises:
   at least one upper horizontal support member;
   at least one lower horizontal support member; and
   a plurality of vertical support members, each fixedly attached at a first end and at a second end to the at least one upper support member and the at least one lower support member, respectively, wherein the plurality of vertical support members is distributed both posteriorly and anteriorly to the upper and lower horizontal support members, wherein each of the plurality of vertical support members contains therein at least one fillable bladder, wherein the at least one bladder of each of the plurality of vertical support members is in fluid communication with a filling means, and wherein each vertical support member is spaced from an adjacent vertical support member by a predetermined distance to provide overall flexibility to the device.

2. The device of claim 1, wherein the region of a human spine to which forces are applied is selected from the group consisting of the cervical region, the thoracic region, and the lumbar region.

3. The device of claim 1, wherein a vertical component of the forces applied to the anatomical region of a spine is in the range of from about 15 to about 100 lbs.

4. The device of claim 1, wherein a vertical component of the forces applied to the anatomical region of a spine is in the range of from about 15 to about 25 pounds.

5. The device of claim 4, wherein the forces are applied to the cervical region of a spine.

6. The device of claim 1, wherein a vertical component of the forces applied to the anatomical region of a spine is in the range of from about 50 to about 100 pounds.

7. The device of claim 6, wherein the forces are applied to the lumbar region of a spine.

8. The device of claim 1, wherein the plurality of vertical support members comprises from four to six members.

9. The device of claim 1, wherein at least one of the horizontal support members comprises an inflatable bladder in fluid communication with an inflation means.

10. The device of claim 1, wherein the device further comprises an inflatable bladder positioned so as to align with the lumbar region of a wearer's spine.

11. The device of claim 1, wherein the filling means is a manual air pump.

12. The device of claim 1, wherein the filling means is a compressed air system.

13. A method for placing a lumbar region of a human spine in a traction condition wherein the lumbar region experiences significantly reduced gravitational stresses, the method comprising the steps of:

(a) securely but removably affixing an upper member of a lumbar traction device to a person whose lumbar spinal region will be placed in the traction condition, wherein the upper member is externally affixed to the person proximal to a rib portion of the person's skeletal anatomy;

(b) securely but removably affixing a lower member of the lumbar traction device to an anatomical region proximal to the person's hips; and (c) filling a plurality of vertical support members, each fixedly attached at a first end and at a second end to the upper member and the lower member of the device, respectively, wherein the plurality of vertical support members is distributed both posteriorly and anteriorly to the upper and lower members, wherein each of the plurality of vertical support members contains therein at least one fillable bladder, wherein the at least one bladder of each of the plurality of vertical support members is in fluid communication with a filling means, and wherein the support members are filled to a pressure effective to create a vertically oriented force in the device equivalent to from about 40% to about 60% of the person's body weight, wherein each vertical support member is spaced from an adjacent vertical support member by a predetermined distance to provide overall flexibility to the device.

* * * * *

UNITED STATES PATENT AND TRADEMARK OFFICE
CERTIFICATE OF CORRECTION

PATENT NO. : 5,724,993
DATED : March 10, 1998
INVENTOR(S) : Dunfee

It is certified that error appears in the above-identified patent and that said Letters Patent is hereby corrected as shown below:

Column 2, line 13, "lumbar" should be italicized.

Column 2, line 20, "cervical" should be italicized.

Column 4, line 13, delete "45 degrees" and insert --45°--.

Column 4, line 25, delete "liking" and insert --lifting--.

Column 4, line 64, "after" should be italicized.

Column 5, lines 13 and 19, "Sports Plus II Belt" should be italicized.

Column 5, line 24, delete "well known" and insert --well-known--.

Column 6, line 33, delete "day-today" and insert --day-to-day--.

Column 6, line 54, "Flaghouse Rehab, Inc. Catalog" should be italicized.

Column 8, line 52, after "PREFERRED" insert --EMBODIMENTS--.

Column 11, line 49, delete "lumber" and insert --lumbar--.

UNITED STATES PATENT AND TRADEMARK OFFICE
CERTIFICATE OF CORRECTION

PATENT NO. : 5,724,993
DATED : March 10, 1998
INVENTOR(S) : Dunfee

It is certified that error appears in the above-identified patent and that said Letters Patent is hereby corrected as shown below:

Column 12, line 20, "n" should be italicized.

Column 12, line 23, after the second occurrence of "+" insert --. . .--.

Column 12, line 32, "n" should be italicized.

Column 12, line 61, "vertically" should be italicized.

Column 12, line 62, after "distribution" insert --of--.

Column 17, line 59, delete 'vertically-directed" and insert --vertically directed--.

Column 18, line 27, delete "invention" and insert --Invention--.

Column 18, line 28, "supra" should be italicized.

Column 18, line 37, delete "intruded" and insert --intended--.

Signed and Sealed this

Twenty-fourth Day of November, 1998

BRUCE LEHMAN

Attest:

Attesting Officer

Commissioner of Patents and Trademarks